United States Patent [19]

Kerns

[11] 4,228,831
[45] Oct. 21, 1980

[54] PROBE AND SYRINGE DRIVE APPARATUS

[75] Inventor: Ralph M. Kerns, Dallas, Tex.

[73] Assignee: Abbott Laboratories, North Chicago, Ill.

[21] Appl. No.: 968,151

[22] Filed: Dec. 11, 1978

[51] Int. Cl.³ .............................................. B65B 3/32
[52] U.S. Cl. .................................. 141/27; 73/423 A; 141/284; 141/392; 422/100
[58] Field of Search ............. 73/423 A; 141/130, 198, 141/284, 329, 392, 388, 18, 21, 25, 27; 250/231.5 E, 561; 340/620; 422/100

[56] References Cited

U.S. PATENT DOCUMENTS

| 398,664 | 2/1889 | Sleeper | 74/660 |
|---|---|---|---|
| 3,251,229 | 5/1966 | Isreeli | 73/423 |
| 3,252,329 | 5/1966 | Heiman | 73/423 |
| 3,550,453 | 12/1970 | Lightner et al. | 73/423 A |
| 3,635,094 | 1/1972 | Oberli | 73/423 A |
| 3,916,186 | 10/1975 | Raser | 250/231.5 E |

Primary Examiner—Frederick R. Schmidt
Attorney, Agent, or Firm—Merriam, Marshall & Bicknell

[57] ABSTRACT

Automatic dispensing apparatus such as used in a chemical analysis system for transferring liquids from sample containers to analysis containers, including a pipet probe assembly with an elongated probe, probe drive means for inserting the probe into the sample and moving the probe assembly between the sample container and analysis container, means for aspirating and dispensing a portion of the sample from the probe into a respective analysis container, an elongated level sensing probe extending downwardly from the probe assembly, with the difference in distance between the tip of the level sensing probe and the tip of the pipet probe defining the amount of penetration of the pipet probe tip below the sample level, and control means, including means responding to the tip of the level sensing probe contacting said sample level to stop the probe drive means thereby minimizing the penetration of the pipet probe tip below the sample level.

3 Claims, 4 Drawing Figures

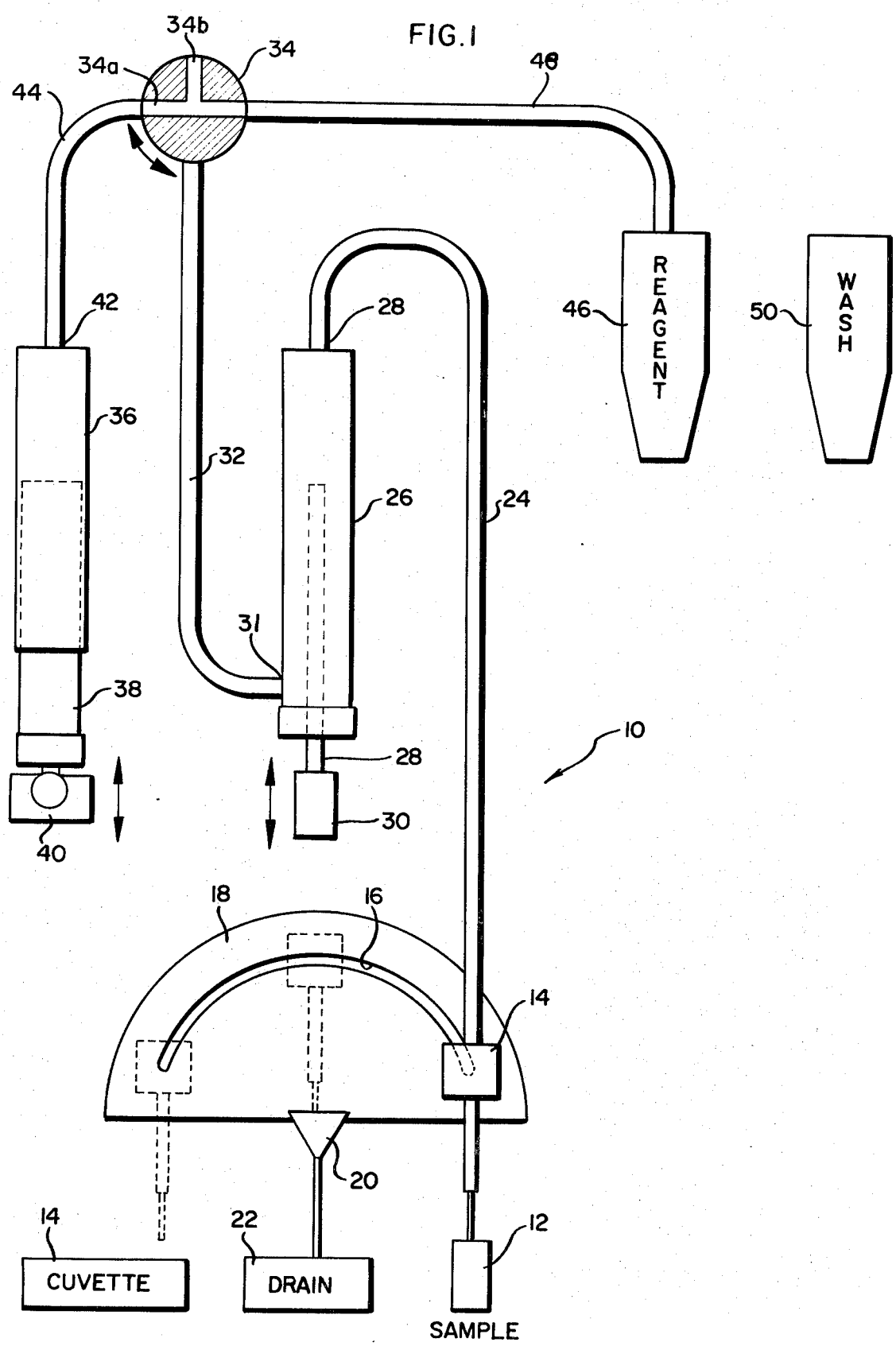

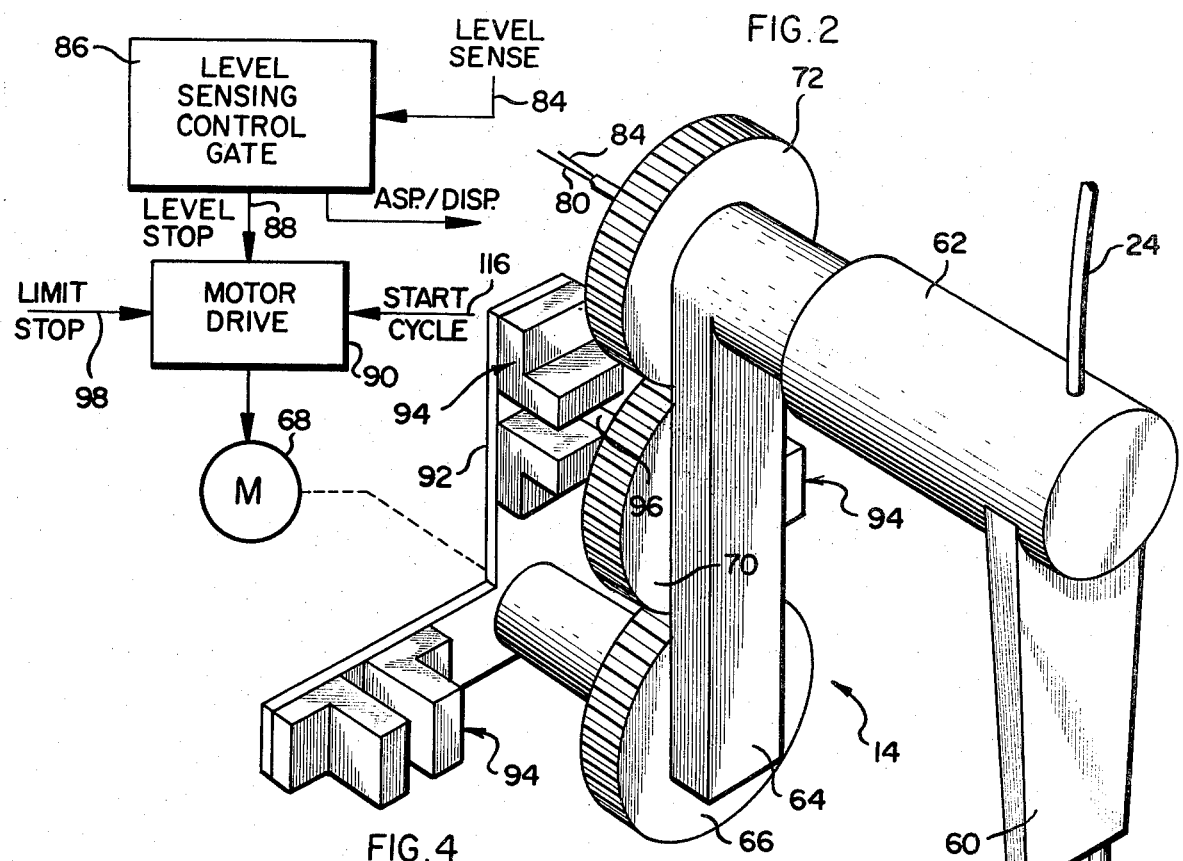
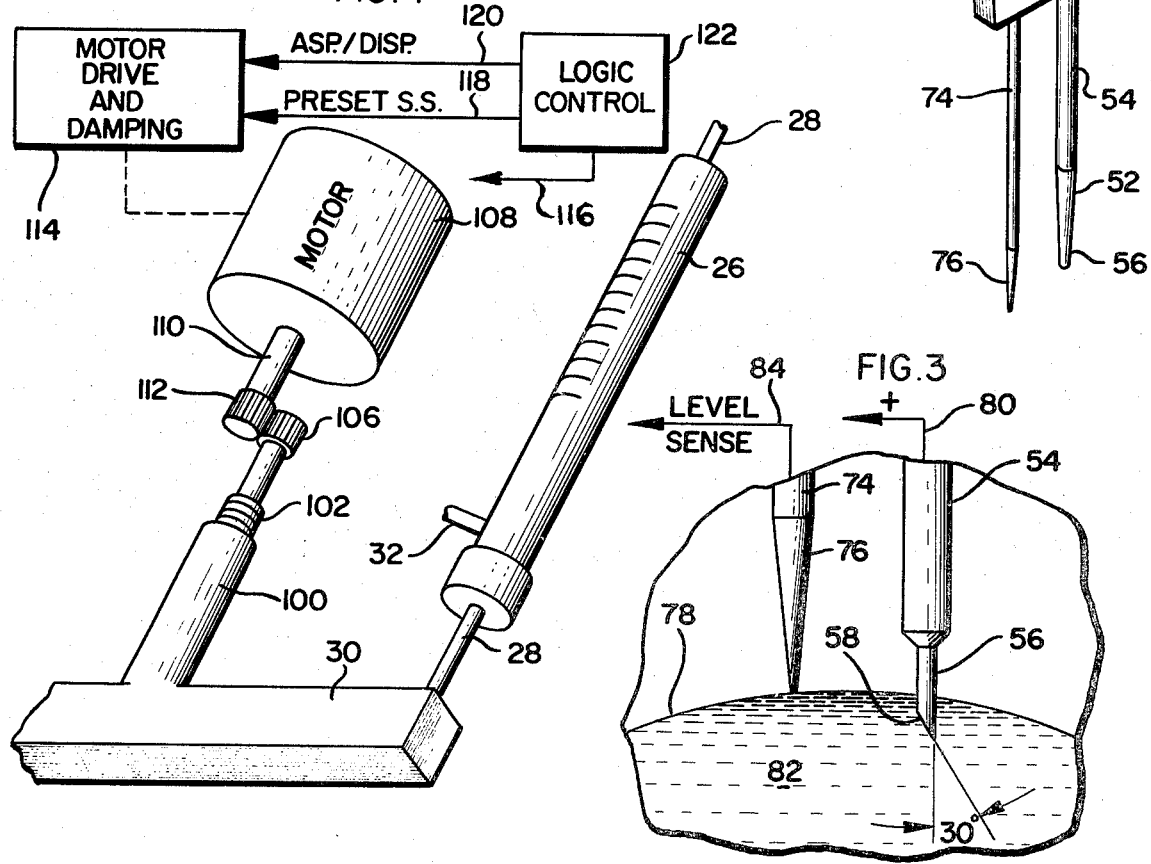

PROBE AND SYRINGE DRIVE APPARATUS

This invention relates to automatic dispensing apparatus for transferring liquids, and more particularly to improvements in such apparatus as used in a chemical analysis system.

BACKGROUND OF THE INVENTION

Reference may be made to the following U.S. Patents of interest: U.S. Pat. Nos. 3,748,044; 3,817,425; 3,900,289; 3,682,305; 3,915,651; 4,042,338; 3,137,172; 3,759,667; and 3,805,998.

Many systems currently exist for automatically performing chemical analysis of blood samples or other organic liquids. Typically, such systems, as shown for example in the aforementioned U.S. Pat. No. 3,748,044, assigned to the same assignee herein, include instrumentation for automatically processing a multiplicity of individual samples by sequentially transferring through a pipet a portion of the individual samples, suitably mixing a reagent, if desired or necessary, and placing the mixture into a respective cuvette. Each of the transferred specimens may then be automatically analyzed by measuring a desired characteristic and the respective measurements presented on visual displays or printed on a recording tape.

It is, of course, desirable to increase the system throughput if possible, i.e., the number of samples which can be processed and measured per unit time, without degrading the instruments' accuracy of measurement. In some systems, care must be taken during loading of the individual, multiple samples to insure that the liquid level in each sample container is the same with respect to a reference level associated with the lower most position of the pipet probe. Since the pipet probe must sequentially enter each of the individual specimens, in such systems, individually setting the level of each sample insures that the pipet probe will only penetrate a minimum distance into the samples. This requires the time-consuming task of manually adjusting the level in each individual sample container, or providing a special mounting in the instrument for each individual sample so that the vertical positions of each sample can be adjusted. In either event, the prior art sample loading procedure is time-consuming or involves additional costly mounting apparatus in order to achieve the accuracy desired. It is to be understood, of course, that failure to control the amount of probe penetration into the respective samples leads to undesired sample carryover, the contamination of samples, and thereby significantly reduces the instrumentation accuracy attainable.

In addition to the minimum probe penetration to guarantee instrumentation accuracy, it is, of course, desired to minimize serum adhesion to the probe in order to increase the instrument's precision of measurement. Furthermore, it has been found that the prior art probe tip structures have a tendency to trap an air bubble at the tip which upon removal of the tip from the sample withdraws a sample bubble. This reduces the desired concentration of sample and thereby adversely affects the measuring accuracy. In addition, it was found that increasing the probe moving speed leads to a hammering effect which tended to undesirably drive reagent from the probe into the sample cup.

SUMMARY OF THE INVENTION

In accordance with the principles of the present invention, there is provided improved liquid transferring apparatus which enables a minimum penetration of the probe into individual specimen containers each having different levels of sample, eliminates air bubble entrapment at the probe tip, minimizes sample adhesion to the probe, and prevents reagent from escaping into the sample as the probe is inserted into the sample container. These improvements enable an increased precision of instrumentation measurements to be attained.

In particular, there is provided a level sensing probe mounted adjacent to the pipet probe and extending from the pipet probe assembly so that there is a difference in the vertical distance between the bottom of the level sensing probe and the pipet probe tip. This vertical distance defines the amount of penetration of the pipet probe tip below a respective sample level. The level sensing probe completes a conductive path from the pipet probe through the sample at the instant when the level sensing probe contacts the sample level. Control means respond to the completion of the conductive path to stop the probe drive, thereby minimizing the penetration of the pipet probe below the level of a respective sample. Thus, in utilizing this aspect of the invention, in an automatic chemical analyzer, multiple samples of differing sample levels can be readily loaded into the system without regard to a reference level or to the need for special mountings as required in the prior art. The probe tip includes a 30° bevel to eliminate air bubble entrapment and a synthetic resin coating applied to the level sensing probe tip to further minimize serum adhesion.

In accordance with another aspect of the present invention, a sample syringe connected to the pipet probe is selectively driven to aspirate air into the probe immediately prior to the probe entering the sample. This forms an air pocket preventing reagent from escaping into the sample container from the probe.

BRIEF DESCRIPTION OF THE DRAWINGS

FIG. 1 schematically illustrates a movable probe assembly and sample and reagent syringes including the interconnecting fluid lines;

FIG. 2 is a perspective view illustrating the probe assembly including the pipet probe, the level sensing probe and the controlled probe drive apparatus;

FIG. 3 is an expanded view illustrating the construction of the level sensing probe and the pipet or serum probe in accordance with one aspect of the present invention; and FIG. 4 is a perspective view illustrating the sample syringe drive components.

DETAILED DESCRIPTION

Referring now to FIG. 1 there is illustrated automatic pipetting or dispensing apparatus 10 useful for instance in conducting chemical analysis on blood samples or other organic liquids. In such instrumentation, a plurality of liquid sample containers 12 are automatically positioned below a pipet probe assembly 14. A portion of the sample is aspirated by the probe assembly for mixing with a suitable reagent if desired and transferring the mixture to a respective cuvette container 14. For convenience, only one of the sample containers 12 and one of the cuvette containers 14 is illustrated in FIG. 1, it being understood that a plurality of such containers is normally present. Current instrumentation includes suitable positioning means for indexing and positioning the respective sample containers and cuvette containers, and such apparatus does not form a portion of the present invention.

Probe assembly 14 is mounted for arcuate positioning within a slot 16 in an instrument front panel 18. In FIG. 1, the probe assembly is shown in the Sample Position. The dashed line indications in FIG. 1 illustrate the positioning of probe assembly 14 at the extreme left Cuvette Position for transferring the aspirated sample portion to the cuvette 14 and at the vertical Home Position for washing the liquids from the probe assembly through funnel 20 and into drain 22.

Fluid line 24 interconnects the probe assembly 14 with a sample syringe 26. The sample syringe 26 is schematically illustrated in FIG. 1 and includes a syringe plunger 28 having one end slidably movable within the syringe 26 and another end rigidly captured within a drive block 30. As will be more particularly described hereinafter, the drive block 30 is movable in incremental steps to aspirate or dispense liquid from the syringe 26 to outlet 28 communicating with the fluid line 24. Syringe inlet 31 is connected to another fluid line 32 which in turn is connected to a three-way valve schematically illustrated as three-way valve 34 in FIG. 1.

A reagent syringe 36 includes a plunger 38 connected to drive block 40 for aspirating or dispensing liquids through syringe output ports 42. A fluid line 44 interconnects the reagent syringe output to three-way valve 34. In the position of the three-way valve shown in FIG. 1, reagent in a supply container 46 can be drawn into reagent syringe 36 through the interconnecting fluid line 48. Another supply container 50 contains a reservoir of suitable cleaning liquid for cleaning the syringe and probe fluid carrying components. Thus, during a wash cycle, one end of the fluid line 48 is removed from the reagent container 46 and inserted into the wash container 50.

Referring now to FIGS. 2 and 3 there is illustrated in greater detail the construction of a preferred embodiment of the probe assembly 14. A pipet or sample probe 52 includes an upper barrel portion 54 and a lower tip portion 56 of reduced diameter with respect to the barrel 54. More particularly, as can be seen from the expanded view of FIG. 3, the bottom of sample probe tip 56 includes a bevel 58. It was found that when utilizing the probe in instrumentation for analysis of blood serum or other organic liquids, it is especially preferred to provide a bevel angle of 30° with respect to the longitudinal axis of the probe tip in order to eliminate air bubble entrapment at the probe tip. It was found, for example, that with a probe tip having a straight end, that is, one at 90° with respect to the tip longitudinal axis, the end tends to withdraw a small liquid bubble as it is raised and leaves the liquid surface. The liquid bubble is formed around an air bubble which is trapped at the probe tip by a straight end tip as it enters the liquid sample. Even probe tips with 45° beveled end tips trapped the air bubble. Also, tips with beveled ends significantly less than about 25° eliminate air bubble entrapment, but undesirably require further sample penetration and are more susceptible to physical damage during use. Thus, it was found that beveled end tips between about 25-35 degrees and preferably a tip at 30° bevel is preferred.

As can be seen from FIG. 2, the sample probe 52 is mounted within and extends from one end 60 of U-shaped member 62. The other end 64 of the U-shaped member 62 is rotatably mounted to a stationary gear 66. End 64 is driven by a motor 68 through a suitable drive shaft, indicated in dashed lines of FIG. 2, which extends through gear 66 and is rigidly mounted to end 64. A pair of engaging, counter-rotating driven gears 70 and 72 each respectively rotatably mounted to the U-shaped member 62 is respectively driven by the rotating end 64 while rotatably engaging the stationary gear 66. Thus, rotation of the end 64 by motor 68 rotates gears 70 and 72, thereby moving the probe assembly 14 in the arcuate slot 16 shown in FIG. 1, while maintaining the probe 52 in vertical position.

A level sensing probe 74 extends from the end 60 generally parallel to the sample probe, and includes a relatively thin upper portion and a tapered, needle-like tip 76. As can be seen most clearly in FIG. 3, the lowermost portion of the sample probe tip 56 extends slightly below the lowermost portion of the level sensing tip 76. Preferably, the difference in extension of the probe tip and the level sensing tip defines the amount of penetration of the probe tip 56 below the sample level 78. Locking means may be provided on end 60 for adjusting and setting the position of the level sensing tip 76 below end 60.

Both the sample probe 52 and the level sensing probe 74 are formed of a metallic conducting member, such as stainless steel, so that a conductive path can be completed between a lead 80 connected to probe 52, through the liquid sample 82, and a lead 84 connected to the level sensing probe 74. Thus, as the lower most portion of level sensing probe tip 76 engages the liquid level 78, a signal is present on the line 84 which can be used to stop motor 68 to control the amount of penetration of probe tip 56 below the level 78. The changed condition on line 84 is coupled to a control gate 86 which responds thereto to provide a stop signal on line 88 coupled to motor drive 90 for deactivating motor 68. Therefore, the sample containers 12 may hold samples of different volumes and differing liquid levels. This significantly reduces the amount of loading time normally required for chemical analysis instruments, and yet maintains the instrumentation reliability since the desired minimum penetration of the probe into the respective samples is retained.

As an example of a constructed embodiment of the present invention found to be particularly useful for analysis of blood serum and other organic liquids, the probe tip upper barrel 54 has an internal diameter of 0.035 inch and a outside diameter of 0.053 inch. The lower portion 56 has an inside diameter of 0.009 inch and an outside diameter of 0.018 inch and a length of 3/16 of an inch. Both the upper and lower portions are formed for stainless steel, with the lower tip 56 being silver brazed onto the upper portion. Alternatively, the sample probe tip could be tapered, as long as the bottom of the taper provides an inside diameter of about 0.009 inch and the tapered end is beveled at between 25-30 degrees. Adhesion of sample 82 to the outside surfaces of probe tip 56 can be substantially reduced by providing a highly polished probe tip outer surface and coating the tip with a synthetic resin preferably one known in the trade as SF2 coating—a porous nickel cobalt impregnated with Teflon, generally available from several suppliers. The level sensing probe 74 is also formed of stainless steel, with the extension difference between the bottom of the sample probe tip and the level sensing tip being maintained at between 0.063–0.123 inch, preferably at 0.093 inch. This tends to maintain the minimum penetration of the sample probe below the level 78 as desired.

A stationary mounted T-frame 92 includes optical limit sensing means 94 at each of the extreme ends of the T-frame, corresponding to the three probe assembly positions shown in FIG. 1. Each of the optical limit sensing assemblies 94 includes a light emitting diode and a light detector operating in conjunction with extension rod 96 protruding from the driven gear 70. In FIG. 2, the probe assembly is shown in the Home Position corresponding to the top most vertical position shown in dashed lines above the drain container 22 in FIG. 1. Upon activating the motor drive 90 and motor 68 to rotate the end 64, thereby rotatably engaging the counter-rotating driven gears 70, 72 with the stationary gear 66, the probe assembly is accurately driven until the extension rod 96 interrupts the optical beam in the optical limit sensing assemblies 94 to provide a Limit Stop signal coupled from the respective limit sensing assembly 94 on line 98 to motor drive 90. At the Sample Position, if no sample level is detected by the aforementioned level sensing means, the associated optical limit switch is operated to provide the Limit Stop signal on line 98. In this case the probe assembly 14 is stopped, and then acurately driven to the Home Position while the next sample container 12 is indexed into the Sample Position. As the probe assembly acurately approaches cuvette 14 at the Cuvette Position, rod 96 interrupts the respective light beam of sensing assembly 94 to couple a Limit Stop signal on line 98.

FIG. 4 illustrates the apparatus for aspirating and dispensing fluids to and from the probe assembly 14. The specific illustration is shown in connection with the sample syringe 26, it being understood that a similar set of components are provided for the reagent syringe 36. In particular, the sample syringe mounting block 30 is illustrated as extending from a hollow cylindrical member 100 having internal threads and being, in turn, threadably mounted on threaded connecting rod 102 with driven gear 106 at the other end. Sample syringe stepping motor 108 has a shaft 110 with driving gear 112 engaging the driven gear 106 so that on each step the connecting rod 102 is rotated a precise amount to linearly displace member 100, thereby raising or lowering plunger 28 in precise amounts. The threaded rod 102 includes precision screw threads such as in a micrometer matching the internal threads of member 100 so as to translate the stepping motor rotational steps into precise linear motion. A conventional stepping motor drive 114 supplies the necessary series of driving pulses to stepping motor 108, and includes damping on the last pulsing step to eliminate any overshoot of the syringe plunger thereby avoiding aspiration of excess sample.

In accordance with another aspect of the present invention, to prevent reagent from escaping into the sample from the probe tip 56 when the probe is inserted into the sample, and thereby undesirably diluting the sample, a preset, three-step movement of the syringe plunger is utilized. In particular, when the probe assembly is in the Home position as shown in FIG. 2, and motor drive 90 receives the Start Cycle signal on line 116, a preset Sample Syringe signal is placed on line 118 into the sample syringe motor drive 114 to drive the sample syringe backwards three steps to aspirate air into the probe tip before the sample probe enters the sample liquid. This forms an air pocket in the probe preventing the reagent from being driven into the sample cup by a hammering effect. Motor drive 114 includes the suitable circuitry for providing the three steps at the time it receives the Preset Sample Syringe signal on line 118.

In operating the apparatus shown in FIGS. 1–4, during aspirating the sample, diluting it with reagent and transferring the mixture to the respective cuvettes the following four steps are utilized:

1. Three-way valve 34 is switched to the position shown in FIG. 1. Probe assembly 14 is at the Home Position above the drain cup 22. Both reagent plunger 38 and sample plunger 28 are in the up position. A Start Cycle signal placed on line 116 activates motor drive 90 to move the probe assembly 14 towards one of the sample containers 12. Immediately, a Preset Sample Syringe signal is placed on line 118 to activate motor drive 114 to drive the syringe plunger 28 down three steps to aspirate a small amount of air into the sample probe before the probe tip enters the sample.

2. As the probe 56 enters the sample cup, the bottom of the level sensing probe tip 76 contacts sample surface 78 to place a Level Sense signal on line 84 gating the control gate 86 to present a Level Stop signal on line 88 to motor drive 90 to stop the probe assembly 14, placing the level sensing probe and the sample probe in the position shown in FIG. 3. An Aspirate Signal is placed on line 120 to stepping motor drive 114 to move the reagent plunger 38 and sample plunger 28 down a desired number of steps, thereby aspirating serum from sample cup 12 through line 24 into the syringe 26, and reagent from reagent container 46 through fluid line 48 and 44 into the reagent syringe 36.

3. Motor drive 90 is activated to move probe assembly 14 through the Home position towards the left-hand position in FIG. 1 above a respective cuvette container 14. Three-way valve 34 is switched to couple line 34a with fluid line 32 and line 34b with line 44.

4. Probe assembly 14 continues to move in arcuate slot 16 until rod 96 interrupts the optical limit switch 94 to place a Limit Stop Signal on line 98. A Dispense Signal is placed on line 120 to operate stepping motor 108 and thereby drive the reagent syringe 38 and sample syringe 28 upwardly a desired number of steps to dispense sample and reagent into the cuvette container 14.

At the completion of this four-step procedure, another sample container 12 and cuvette container 14 is indexed into position so as to bring a new sample and an empty cuvette into position. The four steps indicated above are again repeated, thereby filling the new cuvette with diluted sample. Currently available logic and control means 122 can readily be provided for supplying the properly sequenced timing and control signals for operating the apparatus as described herein.

While particular embodiments of the present invention have been shown and described, it will be obvious to those skilled in the art that various changes and modifications may be made without departing from the invention its its broader aspects. Accordingly, the aim of the appended claims is to cover all such changes and modifications as may fall within the true spirit and scope of the invention.

What is claimed is:

1. In automatic dispensing apparatus for sequentially transferring liquids from a plurality of sample containers having different sample levels to respective analysis containers, including a pipet probe assembly having an elongated pipet probe, probe drive means for inserting said pipet probe into said sample and moving said pipet probe assembly between said sample containers and said analysis containers, aspirating means for aspirating a respective sample into said probe, and dispensing means for dispensing the aspirated sample into said respective analysis containers, the improvement comprising:

said pipet probe having a beveled tip with the angle of said bevel being about 25°-35° with respect to the longitudinal axis of said tip:

an elongated level sensing probe mounted to and extending downwardly from said pipet probe assembly, said level sensing probe including a needle-like tip extending adjacent said pipet probe;

said pipet probe tip extending slightly below said needle-like tip a distance defining the amount of minimal penetration of said pipet probe tip below a respective sample level;

syringe means including a syringe fluidly coupled to said pipet probe, said syringe means including for aspirating a small amount of air into said pipet probe upon signalled movement of said probe assembly towards said sample containers said immediately prior to said pipet probe tip entering said sample to prevent dilution of said sample;

and control means coupled intermediate said syringe means, said level sensing probe and said probe drive means, for signalling said movement of said probe assembly towards said sample container and responding to said needle-like tip contacting the level of a respective sample to stop said probe drive means to minimize the penetration of said pipet probe tip below the level of said respective sample.

2. In automatic dispensing apparatus for sequentially transferring liquids from a plurality of sample containers having different sample levels to respective analysis containers, including a pipet probe assembly having an elongated pipet probe, probe drive means for inserting said pipet probe into said sample and moving said pipet probe assembly between said sample containers and said analysis containers, aspirating means for aspirating a respective sample into said probe, and dispensing means for dispensing the aspirated sample into said respective analysis containers, the improvement comprising:

an elongated level sensing probe mounted to and extending downwardly from said pipet probe assembly, the difference in distance between the tip of said level sensing probe and the tip of said pipet probe defining the amount of penetration of said pipet probe tip below the respective sample level;

control means coupled intermediate said level sensing probe and said probe drive means, including means responding to the tip of said level sensing probe contacting the level of said sample to stop said probe drive means thereby minimizing the penetration of said pipet probe tip below the level of a respective sample;

said pipet probe including a beveled tip with the angle of said bevel being about 25°-35° with respect to the longitudinal axis of said tip; and said aspirating means including means for aspirating air into said pipet probe immediately prior to the tip of said pipet probe penetrating said sample level to prevent dilution of said sample.

3. The improvement of claim 2, wherein said bevel angle is 30°.

* * * * *